(12) United States Patent
Boylan et al.

(10) Patent No.: US 7,938,843 B2
(45) Date of Patent: *May 10, 2011

(54) DEVICES CONFIGURED FROM HEAT SHAPED, STRAIN HARDENED NICKEL-TITANIUM

(75) Inventors: John F. Boylan, Murrieta, CA (US); Keif Fitzgerald, San Jose, CA (US); Zhi Cheng Lin, Mountain View, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 1559 days.

This patent is subject to a terminal disclaimer.

(21) Appl. No.: 10/457,218

(22) Filed: Jun. 9, 2003

(65) Prior Publication Data

US 2003/0199920 A1 Oct. 23, 2003

Related U.S. Application Data

(63) Continuation of application No. 09/896,435, filed on Jun. 29, 2001, now Pat. No. 6,602,272, which is a continuation-in-part of application No. 09/705,422, filed on Nov. 2, 2000.

(51) Int. Cl.
*A61M 29/00* (2006.01)
*A61F 11/00* (2006.01)

(52) U.S. Cl. ........................ 606/200; 606/108

(58) Field of Classification Search ............ 606/200, 606/108, 191, 194, 198; 623/1.11
See application file for complete search history.

(56) References Cited

U.S. PATENT DOCUMENTS

| | | | |
|---|---|---|---|
| 2,738,294 A | 3/1956 | Spence | |
| 2,768,271 A | 10/1956 | Meredith | |
| 3,558,369 A | 1/1971 | Wang et al. | |
| 3,605,725 A | 9/1971 | Bentov | |
| 3,620,212 A | 11/1971 | Fannon et al. | |
| 3,753,700 A | 8/1973 | Harrison et al. | |

(Continued)

FOREIGN PATENT DOCUMENTS

EP 0145166 6/1985

(Continued)

OTHER PUBLICATIONS

Duerig, T. W. et al., Linear Superelasticity in Cold-Worked Ni-Ti, *Engineering Aspects of Shape Memory Alloys*, pp. 414-419 (1990).

(Continued)

*Primary Examiner* — Vy Q Bui
(74) *Attorney, Agent, or Firm* — Workman Nydegger; Jonathan D. Feuchtwang

(57) ABSTRACT

Cold worked nickel-titanium alloys that have linear pseudoelastic behavior without a phase transformation or onset of stress-induced martensite as applied to a medical device having a strut formed body deployed from a sheath is disclosed. In one application, an embolic protection device that employs a linear pseudoelastic nitinol self-expanding strut assembly with a small profile delivery system for use with interventional procedures is disclosed. The expandable strut assembly is covered with a filter element and both are compressed into a restraining sheath for delivery to a deployment site downstream and distal to an interventional procedure. Once at the desired site, the restraining sheath is retracted to deploy the embolic protection device, which captures flowing emboli generated during the interventional procedure. Linear pseudoelastic nitinol is used in the medical device as distinct from non-linear pseudoelastic (i.e., superelastic) nitinol.

4 Claims, 3 Drawing Sheets

U.S. PATENT DOCUMENTS

| | | | |
|---|---|---|---|
| 3,890,977 A | 6/1975 | Wilson | |
| 3,953,253 A | 4/1976 | Clark | |
| 4,019,899 A | 4/1977 | Negishi et al. | |
| 4,037,324 A | 7/1977 | Andreasen | |
| 4,069,226 A | 1/1978 | Kablaoui et al. | |
| 4,144,057 A | 3/1979 | Melton et al. | |
| 4,233,690 A | 11/1980 | Akins | |
| 4,283,233 A | 8/1981 | Goldstein et al. | |
| 4,304,613 A | 12/1981 | Wang et al. | |
| 4,310,354 A | 1/1982 | Fountain et al. | |
| 4,323,071 A | 4/1982 | Simpson et al. | |
| 4,386,971 A | 6/1983 | Melton et al. | |
| 4,390,599 A | 6/1983 | Broyles | |
| 4,411,655 A | 10/1983 | Schreck | |
| 4,425,908 A | 1/1984 | Simon | |
| 4,427,000 A | 1/1984 | Ueda | |
| 4,439,185 A | 3/1984 | Lundquist | |
| 4,503,569 A | 3/1985 | Dotter | |
| 4,505,767 A | 3/1985 | Quin | |
| 4,512,338 A | 4/1985 | Balko et al. | |
| 4,516,972 A | 5/1985 | Samson | |
| 4,518,444 A | 5/1985 | Albrecht et al. | |
| 4,533,411 A | 8/1985 | Melton | |
| 4,538,622 A | 9/1985 | Samson et al. | |
| 4,554,929 A | 11/1985 | Samson et al. | |
| 4,565,589 A | 1/1986 | Harrison | |
| 4,580,568 A | 4/1986 | Gianturco | |
| 4,582,181 A | 4/1986 | Samson | |
| 4,616,652 A | 10/1986 | Simpson | |
| 4,631,094 A | 12/1986 | Simpson et al. | |
| 4,638,805 A | 1/1987 | Powell | |
| 4,665,906 A | 5/1987 | Jervis | |
| 4,740,253 A | 4/1988 | Simpson et al. | |
| 4,748,986 A | 6/1988 | Morrison et al. | |
| 4,768,507 A | 9/1988 | Fischell et al. | |
| 4,770,725 A | 9/1988 | Simpson et al. | |
| 4,776,844 A | 10/1988 | Ueda | |
| 4,793,350 A | 12/1988 | Mar et al. | |
| 4,827,941 A | 5/1989 | Taylor et al. | |
| 4,846,573 A | 7/1989 | Taylor et al. | |
| 4,856,516 A | 8/1989 | Hillstead | |
| 4,865,663 A | 9/1989 | Tuominen et al. | |
| 4,875,489 A | 10/1989 | Messner et al. | |
| 4,881,981 A | 11/1989 | Thoma et al. | |
| 4,894,100 A | 1/1990 | Yamauchi et al. | |
| 4,925,445 A | 5/1990 | Sakamoto et al. | |
| 4,935,068 A | 6/1990 | Duerig | |
| 4,943,326 A | 7/1990 | Ozawa et al. | |
| 4,969,890 A | 11/1990 | Sugita et al. | |
| 4,984,581 A | 1/1991 | Stice | |
| 4,991,602 A | 2/1991 | Amplatz et al. | |
| 5,001,446 A | 3/1991 | Tsuji et al. | |
| 5,002,563 A | 3/1991 | Pyka et al. | |
| 5,025,799 A | 6/1991 | Wilson | |
| 5,044,947 A | 9/1991 | Sachdeva et al. | |
| 5,067,489 A | 11/1991 | Lind | |
| 5,067,957 A | 11/1991 | Jervis | |
| 5,069,226 A | 12/1991 | Yamauchi et al. | |
| 5,092,877 A | 3/1992 | Pinchuk | |
| 5,108,523 A | 4/1992 | Peterseim et al. | |
| 5,114,504 A | 5/1992 | AbuJudom, II et al. | |
| 5,117,838 A | 6/1992 | Palmer et al. | |
| 5,120,308 A | 6/1992 | Hess | |
| 5,135,503 A | 8/1992 | Abrams | |
| 5,143,085 A | 9/1992 | Wilson | |
| 5,171,383 A | 12/1992 | Sagaye et al. | |
| 5,188,621 A | 2/1993 | Samson | |
| 5,190,546 A | 3/1993 | Jervis | |
| 5,201,901 A | 4/1993 | Harada et al. | |
| 5,230,348 A | 7/1993 | Ishibe et al. | |
| 5,230,349 A | 7/1993 | Langberg | |
| 5,234,458 A | 8/1993 | Metais | |
| 5,238,004 A | 8/1993 | Sahatjian et al. | |
| 5,243,996 A | 9/1993 | Hall | |
| 5,271,975 A | 12/1993 | Solano | |
| 5,292,331 A | 3/1994 | Boneau | |
| 5,318,527 A | 6/1994 | Hyde et al. | |
| 5,341,815 A | 8/1994 | Cofone et al. | |
| 5,341,818 A | 8/1994 | Abrams et al. | |
| 5,345,937 A | 9/1994 | Middleman et al. | |
| 5,345,945 A | 9/1994 | Hodgson et al. | |
| 5,350,398 A | 9/1994 | Pavcnik et al. | |
| 5,350,419 A * | 9/1994 | Bendel et al. | 607/132 |
| 5,354,623 A | 10/1994 | Hall | |
| 5,368,049 A | 11/1994 | Raman et al. | |
| 5,411,476 A | 5/1995 | Abrams et al. | |
| 5,458,615 A | 10/1995 | Klemm et al. | |
| 5,465,717 A | 11/1995 | Imran et al. | |
| 5,486,183 A | 1/1996 | Middleman et al. | |
| 5,507,766 A | 4/1996 | Kugo et al. | |
| 5,509,923 A | 4/1996 | Middleman et al. | |
| 5,514,154 A | 5/1996 | Lau et al. | |
| 5,534,007 A | 7/1996 | St. Germain et al. | |
| 5,549,626 A | 8/1996 | Miller et al. | |
| 5,562,641 A | 10/1996 | Flomenblit et al. | |
| 5,569,295 A | 10/1996 | Lam | |
| 5,573,520 A | 11/1996 | Schwartz et al. | |
| 5,597,378 A | 1/1997 | Jervis | |
| 5,607,444 A | 3/1997 | Lam | |
| 5,611,874 A | 3/1997 | Zadno-Azizi et al. | |
| 5,630,840 A | 5/1997 | Mayer | |
| 5,632,746 A | 5/1997 | Middleman et al. | |
| 5,637,089 A | 6/1997 | Abrams et al. | |
| 5,641,364 A | 6/1997 | Golberg et al. | |
| 5,643,312 A | 7/1997 | Fischell et al. | |
| 5,667,522 A | 9/1997 | Flomenblit et al. | |
| 5,690,644 A | 11/1997 | Yurek et al. | |
| 5,695,111 A | 12/1997 | Nanis et al. | |
| 5,713,853 A | 2/1998 | Clark et al. | |
| 5,720,300 A | 2/1998 | Fagan et al. | |
| 5,720,754 A | 2/1998 | Middleman et al. | |
| 5,749,370 A | 5/1998 | Brooks et al. | |
| 5,749,870 A | 5/1998 | Gloth et al. | |
| 5,749,879 A | 5/1998 | Middleman et al. | |
| 5,759,192 A | 6/1998 | Saunders | |
| 5,766,218 A | 6/1998 | Arnott | |
| 5,776,114 A | 7/1998 | Frantzen et al. | |
| 5,780,807 A | 7/1998 | Saunders | |
| 5,810,874 A | 9/1998 | Lefebvre | |
| 5,820,628 A | 10/1998 | Middleman et al. | |
| 5,833,631 A | 11/1998 | Nguyen | |
| 5,836,966 A | 11/1998 | St. Germain | |
| 5,836,968 A | 11/1998 | Simon et al. | |
| 5,837,313 A | 11/1998 | Ding et al. | |
| 5,843,244 A | 12/1998 | Pelton et al. | |
| 5,865,768 A | 2/1999 | Orr | |
| 5,876,356 A | 3/1999 | Viera et al. | |
| 5,876,434 A | 3/1999 | Flomenblit et al. | |
| 5,885,381 A | 3/1999 | Mitose et al. | |
| 5,891,191 A | 4/1999 | Stinson | |
| 5,902,317 A | 5/1999 | Kleshinski et al. | |
| 5,904,690 A | 5/1999 | Middleman et al. | |
| 5,907,893 A | 6/1999 | Zadno-Azizi et al. | |
| 5,910,154 A | 6/1999 | Tsugita et al. | |
| 5,911,734 A | 6/1999 | Tsugita et al. | |
| 5,922,393 A | 7/1999 | Jayaraman | |
| 5,927,345 A | 7/1999 | Samson | |
| 5,931,819 A | 8/1999 | Fariabi | |
| 5,951,793 A | 9/1999 | Mitose et al. | |
| 5,964,770 A | 10/1999 | Flomenblit et al. | |
| 5,976,153 A | 11/1999 | Fischell et al. | |
| 5,980,471 A | 11/1999 | Jafari | |
| 5,980,566 A | 11/1999 | Alt et al. | |
| 5,989,280 A | 11/1999 | Euteneuer et al. | |
| 6,001,123 A | 12/1999 | Lau | |
| 6,004,330 A * | 12/1999 | Middleman et al. | 606/127 |
| 6,004,629 A | 12/1999 | Madigan | |
| 6,007,558 A | 12/1999 | Ravenscroft et al. | |
| RE36,628 E | 3/2000 | Sagae et al. | |
| 6,051,021 A | 4/2000 | Frid | |
| 6,053,992 A | 4/2000 | Wu et al. | |
| 6,059,738 A | 5/2000 | Stoltze et al. | |
| 6,059,810 A | 5/2000 | Brown et al. | |
| 6,066,149 A | 5/2000 | Samson et al. | |
| 6,068,610 A | 5/2000 | Ellis et al. | |
| 6,068,623 A | 5/2000 | Zadno-Azizi et al. | |
| 6,077,287 A | 6/2000 | Taylor et al. | |

| | | | | | | |
|---|---|---|---|---|---|---|
| 6,077,295 | A | 6/2000 | Limon et al. | 7,175,655 B1 | 2/2007 | Molaei |
| 6,086,610 | A | 7/2000 | Duerig et al. | 7,244,319 B2 | 7/2007 | Abrams et al. |
| 6,096,175 | A | 8/2000 | Roth | 7,258,753 B2 | 8/2007 | Abrams et al. |
| 6,099,549 | A | 8/2000 | Bosma et al. | 2001/0007953 A1 | 7/2001 | Duerig et al. |
| 6,106,642 | A | 8/2000 | DiCarlo et al. | 2001/0039446 A1 | 11/2001 | Edwin et al. |
| 6,129,739 | A | 10/2000 | Khosravi | 2001/0039449 A1 | 11/2001 | Johnson et al. |
| 6,131,266 | A | 10/2000 | Saunders | 2001/0047202 A1 | 11/2001 | Slaikeu et al. |
| 6,137,060 | A | 10/2000 | Avellanet | 2001/0049549 A1 | 12/2001 | Boylan et al. |
| 6,152,946 | A | 11/2000 | Broome et al. | 2002/0010481 A1 | 1/2002 | Jayaraman et al. |
| 6,165,140 | A | 12/2000 | Ferrera | 2002/0046785 A1 | 4/2002 | Abrams et al. |
| 6,165,195 | A | 12/2000 | Wilson et al. | 2002/0062092 A1 | 5/2002 | Muni et al. |
| 6,165,292 | A | 12/2000 | Abrams et al. | 2002/0068954 A1 | 6/2002 | Foster |
| 6,168,571 | B1 | 1/2001 | Solar et al. | 2002/0082681 A1 | 6/2002 | Boylan et al. |
| 6,171,327 | B1 | 1/2001 | Daniel et al. | 2002/0087099 A1 | 7/2002 | Nanis et al. |
| 6,171,334 | B1 | 1/2001 | Cox | 2002/0121316 A1 | 9/2002 | Abrams et al. |
| 6,179,859 | B1 | 1/2001 | Bates et al. | 2002/0138129 A1 | 9/2002 | Armstrong et al. |
| 6,183,409 | B1 | 2/2001 | Armini | 2002/0193827 A1 | 12/2002 | McGuckin, Jr. et al. |
| 6,190,332 | B1 | 2/2001 | Muni et al. | 2003/0004536 A1 | 1/2003 | Boylan et al. |
| 6,210,312 | B1 | 4/2001 | Nagy | 2003/0036794 A1 | 2/2003 | Ragheb et al. |
| 6,217,567 | B1 | 4/2001 | Zadno-Azizi et al. | 2003/0040772 A1 | 2/2003 | Hyodoh et al. |
| 6,217,589 | B1 | 4/2001 | McAlister | 2003/0055449 A1 | 3/2003 | Lee et al. |
| 6,245,103 | B1 | 6/2001 | Stinson | 2003/0055484 A1 | 3/2003 | Lau et al. |
| 6,257,513 | B1 | 7/2001 | Cockerham et al. | 2003/0069492 A1 | 4/2003 | Abrams et al. |
| 6,264,671 | B1 | 7/2001 | Stack et al. | 2003/0069521 A1 | 4/2003 | Reynolds et al. |
| 6,277,139 | B1 | 8/2001 | Levinson et al. | 2003/0120181 A1 | 6/2003 | Toma et al. |
| 6,280,539 | B1 | 8/2001 | Abrams et al. | 2003/0127158 A1 | 7/2003 | Abrams et al. |
| 6,287,336 | B1 | 9/2001 | Globerman et al. | 2003/0158575 A1 | 8/2003 | Boylan et al. |
| 6,306,141 | B1 | 10/2001 | Jervis | 2004/0084115 A1 | 5/2004 | Abrams et al. |
| 6,312,454 | B1 | 11/2001 | Stöockel et al. | 2004/0093009 A1 | 5/2004 | Denison et al. |
| 6,312,455 | B2 | 11/2001 | Duerig et al. | 2004/0158281 A1 | 8/2004 | Boylan et al. |
| 6,322,847 | B1 | 11/2001 | Zhong et al. | 2004/0172055 A1 | 9/2004 | Huter et al. |
| 6,325,824 | B2 | 12/2001 | Limon | 2004/0220608 A1 | 11/2004 | D'Aquanni et al. |
| 6,329,069 | B1 | 12/2001 | Azizi et al. | 2005/0038500 A1 | 2/2005 | Boylan et al. |
| 6,346,116 | B1 | 2/2002 | Brooks et al. | 2006/0086440 A1 | 4/2006 | Boylan et al. |
| 6,352,515 | B1 | 3/2002 | Anderson et al. | 2006/0212068 A1 | 9/2006 | Boylan |
| 6,358,556 | B1 | 3/2002 | Ding et al. | 2007/0233179 A1 | 10/2007 | Brady et al. |
| 6,371,970 | B1 | 4/2002 | Khosravi et al. | 2007/0239259 A1 | 10/2007 | Boylan |
| 6,375,458 | B1 | 4/2002 | Moorleghem et al. | 2007/0249965 A1 | 10/2007 | Abrams et al. |
| 6,375,628 | B1 | 4/2002 | Zadno-Azizi et al. | 2008/0027532 A1 | 1/2008 | Boylan et al. |
| 6,375,629 | B1 | 4/2002 | Muni et al. | 2009/0098013 A1 | 4/2009 | Boylan et al. |
| 6,379,369 | B1 | 4/2002 | Abrams et al. | 2009/0248130 A1 | 10/2009 | Boylan |
| 6,380,457 | B1 | 4/2002 | Yurek et al. | 2010/0125329 A1 | 5/2010 | Lin et al. |
| 6,390,993 | B1 | 5/2002 | Cornish et al. | | | |
| 6,391,502 | B1 | 5/2002 | Anderson et al. | FOREIGN PATENT DOCUMENTS | | |
| 6,402,761 | B2 | 6/2002 | McAlister | EP | 0199715 | 10/1986 |
| 6,419,692 | B1 | 7/2002 | Yang et al. | EP | 0340304 | 11/1989 |
| 6,419,693 | B1 | 7/2002 | Fariabi | EP | 0395098 | 10/1990 |
| 6,428,634 | B1 | 8/2002 | Besselink et al. | EP | 0480427 | 4/1992 |
| 6,432,116 | B1 | 8/2002 | Callister et al. | EP | 0484805 | 5/1992 |
| 6,447,523 | B1 | 9/2002 | Middleman et al. | EP | 0491349 | 6/1992 |
| 6,451,047 | B2 | 9/2002 | McCrea et al. | EP | 0515078 | 11/1992 |
| 6,451,052 | B1 | 9/2002 | Burmeister et al. | EP | 0520073 | 12/1992 |
| 6,458,145 | B1 | 10/2002 | Ravenscroft et al. | EP | 0550258 | 7/1993 |
| 6,461,453 | B1 | 10/2002 | Abrams et al. | EP | 550288 | 7/1993 |
| 6,468,230 | B2 | 10/2002 | Muni et al. | EP | 0569166 | 11/1993 |
| 6,500,182 | B2 | 12/2002 | Foster | EP | 0791340 | 8/1997 |
| 6,508,803 | B1 | 1/2003 | Horikawa et al. | EP | 0804934 | 11/1997 |
| 6,509,094 | B1 | 1/2003 | Shah et al. | EP | 0806220 | 11/1997 |
| 6,533,805 | B1 | 3/2003 | Jervis | EP | 0812928 | 12/1997 |
| 6,554,848 | B2 | 4/2003 | Boylan et al. | EP | 0815803 | 1/1998 |
| 6,558,405 | B1 | 5/2003 | McInnes | EP | 0873734 | 10/1998 |
| 6,572,646 | B1 | 6/2003 | Boylan et al. | EP | 0879614 | 11/1998 |
| 6,582,461 | B1 | 6/2003 | Burmeister et al. | EP | 0968688 | 1/2000 |
| 6,592,559 | B1 * | 7/2003 | Pakter et al. ............... 604/272 | EP | 1 027 906 A2 | 8/2000 |
| 6,592,570 | B2 | 7/2003 | Abrams et al. | EP | 1426071 | 6/2004 |
| 6,602,208 | B2 | 8/2003 | Jafari | JP | 44-31704 | 12/1969 |
| 6,602,228 | B2 | 8/2003 | Nanis et al. | JP | 44-32286 | 12/1969 |
| 6,602,272 | B2 | 8/2003 | Boylan et al. | JP | 53-12759 | 2/1978 |
| 6,626,937 | B1 | 9/2003 | Cox | JP | 55-164304 | 12/1980 |
| 6,638,372 | B1 | 10/2003 | Abrams et al. | JP | 57-89859 | 6/1982 |
| 6,682,608 | B2 | 1/2004 | Abrams et al. | JP | 58-161746 | 9/1983 |
| 6,706,053 | B1 | 3/2004 | Boylan et al. | JP | 60-145155 | 7/1985 |
| 6,755,845 | B2 | 6/2004 | Kieturakis et al. | JP | 60-138547 | 9/1985 |
| 6,755,855 | B2 | 6/2004 | Yurek et al. | JP | 60-248856 | 12/1985 |
| 6,824,560 | B2 | 11/2004 | Pelton | JP | 61-84361 | 4/1986 |
| 6,830,638 | B2 | 12/2004 | Boylan et al. | JP | 61-183455 | 8/1986 |
| 6,855,161 | B2 | 2/2005 | Boylan et al. | JP | 62-199757 | 9/1987 |
| 7,037,320 | B2 | 5/2006 | Brady | JP | 62-199758 | 9/1987 |
| 7,128,757 | B2 | 10/2006 | Boylan et al. | JP | 62-235449 | 10/1987 |

| | | |
|---|---|---|
| JP | 63-171570 | 7/1988 |
| JP | 64-49571 | 2/1989 |
| JP | 1-124473 | 5/1989 |
| JP | 1-242763 | 9/1989 |
| JP | 252467 | 10/1990 |
| JP | 2289265 | 11/1990 |
| JP | 2289266 | 11/1990 |
| JP | 4-9162 | 1/1992 |
| JP | 50-19512 | 1/1993 |
| JP | 5-92044 | 4/1993 |
| JP | 6-83726 | 3/1994 |
| JP | 61-08431 | 4/1994 |
| JP | 09-215753 | 8/1997 |
| JP | 11-76420 | 3/1999 |
| JP | 2000-140124 | 5/2000 |
| JP | 03-295562 | 10/2003 |
| JP | 4-292174 | 10/2004 |
| WO | WO 89/10088 | 11/1989 |
| WO | WO 89/12175 | 12/1989 |
| WO | WO 90/13329 | 11/1990 |
| WO | WO 91/15152 | 10/1991 |
| WO | WO 92/05828 | 4/1992 |
| WO | WO 93/19803 | 10/1993 |
| WO | WO 00/19800 | 7/1995 |
| WO | WO 97/24978 | 7/1997 |
| WO | WO 97/38747 | 10/1997 |
| WO | WO 98/20801 | 5/1998 |
| WO | WO 98/20810 | 5/1998 |
| WO | WO 99/32051 | 7/1999 |
| WO | WO 99/44542 | 9/1999 |
| WO | WO 00/04846 | 2/2000 |
| WO | WO 00/49970 | 8/2000 |
| WO | WO 00/67665 | 11/2000 |
| WO | WO 00/67668 | 11/2000 |
| WO | WO 00/69359 | 11/2000 |
| WO | WO 01/39695 | 6/2001 |
| WO | WO 01/41859 | 6/2001 |
| WO | WO 01/82830 | 11/2001 |
| WO | WO 02/36841 A2 | 5/2002 |
| WO | WO 02/051462 | 7/2002 |
| WO | WO 02/102281 | 12/2002 |
| WO | WO 03/02166 | 1/2003 |
| WO | WO 03/028796 | 4/2003 |
| WO | WO 03/097148 | 11/2003 |
| WO | WO 2004/033016 | 4/2004 |
| WO | WO 2004/098458 | 11/2004 |
| WO | WO 2005/102407 | 11/2005 |
| WO | WO 2006/081011 | 8/2006 |

OTHER PUBLICATIONS

Duerig, T. W. et al., An Introduction to Martensite and Shape Memory, *Engineering Aspects of Shape Memory Alloys*, pp. 3-20 (1990).
Zhang, C. S. et al., Pseudoelasticity of Near-Equiatomic Ni-Ti Shape Memory Alloy, *Proceedings of The First International Conference on Shape Memory and Superelastic Technologies*, pp. 383-388 (1994).
Duerig, T.W. et al., Ti-Ni Shape Memory Alloys, Materials Properties Handbook Titanium Alloys, *Advanced Materials*, 1035-1048, ASM International (1994).
Khmelevskaya, I.Y. et al., Thermomechanical Treatment of Ti-Ni Shape Memory Alloys: Transofrmations, Structure and Propertues, *First European Conference on Shape Memory and Superelastic Technologies SMST-99*, 1-8 (Sep. 5-9, 1999).
Nishida, M. et al., Precipitation Processes in Near-Equiatomic TiNi Shape Memory Alloys, *Metallurgical Transactions*, 17A, 1505-1515 (Sep. 1986).
Simon, M. et al., A Vena Cava Filter Using Thermal Shape Memory Alloy, *Radiology*, 125, 89-94 (Oct. 1977).
U.S. Appl. No. 09/705,422, filed Nov. 2, 2000, Boylan et al.
U.S. Appl. No. 10/327,371, filed Dec. 19, 2002, Lin.
U.S. Appl. No. 10/374,632, filed Feb. 25, 2003, Boylan et al.
Cold Laser Beam Cuts Clean http://www.photonics.com/Spectra/Applications/oct02/appsCold.asp (Oct. 2002), printed Dec. 08, 2002 (2 pages).
Comparison Water jet-Laser-Microjet©, http://synova.vhosts.cogito.nimag.net/tech comparison. html, printed Dec. 8, 2002 (5 pages).
Duerig, T.W. et al., an Engineer's Perspective of Pseudoelasticity, *The Mechanisms of Pseudoelasticity*, 369-393 (1990).
*Fundamental characteristics of nickel-titanium shape memory alloy*, http://herkules.oulu.fi/isbn9514252217/html/x317.html, printed Oct. 01, 2002 (12 pages).
Hosada et al., "Phase Transformation of Ti-Ni Containing Platinum-Group Metals," Mat. Res. Soc. Symp. Proc., Materials Research Society, Vo. 753, pp. BB5.51.1-BB5.51.6 (2003).
Inoue et al., *Viscoelasticity and Morphology of Soft Polycarbonate as a Substitute for Poly(vinyl chloride)*, ICR Annual Report, 7:24-25 (2000).
*Material properties for part design*, http://www.scudc.scu.edu/cmdoc/dg_doc/develop/material/property/a2200002.htm, printed Oct. 01, 2002 (13 pages).
Pelton, A.R. et al., Optimisation of Processing and Properties of Medical Grade Nitinol Wire, Min Invas Ther & Allied Technol 2000, 9(1), 107-118.
Ren et al., *Origin of rubber-like behaviour in metal alloys*, Nature, 389:579-582 (Oct. 1997).
Russell et al. *Improved NiTi Alloys for Medical Applications*, SMST-97: Proceedings of the Second International Conference on Shape Memory and Superelastic Technologies, pp. 429-436 (1997).
Schetky, L. McDonald, Shape Memory Alloys, *Scientific American*, pp. 74-82 (Nov. 1979).
Stöckel, D. et al., Legierungen mit Formgedächtnis, *Kontakt Studium*, vol. 259, pp. 174-187 (1988).
Stress Strain Behavior of Polymers, http://www.eng.uc.udu/~gbeaucag/Classes/Characterization/StressStrainhtml/StressStrain.html,printed Oct. 01, 2002 (12 pages).
*The Video Extensometer*, http://www.sensorland.com/HowPage050.html., printed Dec. 8, 2002 (8 pages).
*Trade-in Program-Upgrade to NEW Instron Technology!*, http://www.instron.com/Universal testing/tradin.asp, printed Dec. 08, 2002 (2 pages).
U.S. Appl. No. 09/705,422, mailed Sep. 10, 2003, Office Action.
U.S. Appl. No. 09/705,422, mailed Mar. 4, 2004, Office Action.
U.S. Appl. No. 09/705,422, mailed Jul. 27, 2004, Office Action.
U.S. Appl. No. 09/705,422, mailed Nov. 15, 2004, Office Action.
U.S. Appl. No. 09/705,422, mailed Nov. 2, 2005, Office Action.
U.S. Appl. No. 09/705,422, mailed Mar. 21, 2006, Office Action.
U.S. Appl. No. 09/705,422, mailed Aug. 24, 2006, Office Action.
U.S. Appl. No. 09/705,422, mailed Apr. 3, 2007, Office Action.
U.S. Appl. No. 09/705,422, mailed Nov. 14, 2007, Office Action.
U.S. Appl. No. 09/705,422, mailed Mar. 17, 2008, Office Action.
U.S. Appl. No. 09/705,422, mailed Jan. 22, 2009, Office Action.
U.S. Appl. No. 09/705,422, mailed Jul. 10, 2009, Office Action.
U.S. Appl. No. 09/705,422, mailed Jan. 19, 2010, Office Action.
U.S. Appl. No. 09/896,435, mailed Mar. 21, 2003, Notice of Allowance.
U.S. Appl. No. 09/896,435, mailed Jul. 17, 2003, Issue Notification.
U.S. Appl. No. 10/327,371, mailed Oct. 19, 2005, Office Action.
U.S. Appl. No. 10/327,371, mailed Apr. 20, 2006, Office Action.
U.S. Appl. No. 10/327,371, mailed Sep. 27, 2006, Office Action.
U.S. Appl. No. 10/327,371, mailed Mar. 6, 2007, Office Action.
U.S. Appl. No. 10/327,371, mailed May 24, 2007, Office Action.
U.S. Appl. No. 10/327,371, mailed Oct. 9, 2007, Office Action.
U.S. Appl. No. 10/327,371, mailed Jun. 27, 2008, Office Action.
U.S. Appl. No. 10/327371, mailed Nov. 26, 2008, Office Action.
U.S. Appl. No. 10/327371, mailed Jul. 8, 2009, Office Action.
U.S. Appl. No. 10/374632, mailed Jun. 14, 2004, Office Action.
U.S. Appl. No. 07/629,381, mailed Dec. 30, 1991, Office Action.
U.S. Appl. No. 07/629,381, mailed Apr. 23, 1992, Office Action.
U.S. Appl. No. 07/629,381, mailed Dec. 1, 1992, Office Action.
U.S. Appl. No. 07/994,679, mailed Jun. 17, 1993, Office Action.
U.S. Appl. No. 07/994,679, mailed Oct. 1, 1993, Office Action.
U.S. Appl. No. 07/994,679, mailed Dec. 21, 1993, Notice of Allowance.
U.S. Appl. No. 08/071,322, mailed Nov. 1, 1993, Office Action.
U.S. Appl. No. 08/071,322, mailed Apr. 4, 1994, Office Action.
U.S. Appl. No. 08/071,322, mailed Aug. 30, 1994, Office Action.
U.S. Appl. No. 08/071,322, mailed Nov. 23, 1994, Notice of Allowance.
U.S. Appl. No. 08/212,431, mailed Jan. 10, 1995, Office Action.

U.S. Appl. No. 08/212,431, mailed Aug. 22, 1995, Notice of Allowance.
U.S. Appl. No. 08/276,082, mailed Aug. 30, 1996, Office Action.
U.S. Appl. No. 08/276,082, mailed Mar. 3, 1997, Office Action.
U.S. Appl. No. 08/276,082, mailed Apr. 4, 1997, Notice of Allowance.
U.S. Appl. No. 08/432,028, mailed Apr. 15, 1996, Office Action.
U.S. Appl. No. 08/432,028, mailed Sep. 3, 1996, Office Action.
U.S. Appl. No. 08/484,218, mailed May 28, 1996, Office Action.
U.S. Appl. No. 08/484,218, mailed Sep. 16, 1996, Office Action.
U.S. Appl. No. 08/484,218, mailed Mar. 14, 1997, Office Action.
U.S. Appl. No. 08/484,218, mailed Dec. 1, 1997, Office Action.
U.S. Appl. No. 08/484,218, mailed Sep. 17, 1998, Notice of Allowance.
U.S. Appl. No. 08/484,218, mailed Sep. 7, 1999, Office Action.
U.S. Appl. No. 08/484,218, mailed Mar. 15, 2000, Notice of Allowance.
U.S. Appl. No. 08/527,650, mailed Dec. 11, 1995, Notice of Allowance.
U.S. Appl. No. 08/598,639, mailed Nov. 13, 1996, Notice of Allowance.
U.S. Appl. No. 08/982,725, mailed Feb. 25, 1999, Office Action.
U.S. Appl. No. 08/982,725, mailed Aug. 11, 1999, Office Action.
U.S. Appl. No. 08/982,725, mailed Feb. 28, 2000, Office Action.
U.S. Appl. No. 08/982,725, mailed Aug. 15, 2000, Office Action.
U.S. Appl. No. 08/982,725, mailed Jul. 18, 2001, Notice of Allowance.
U.S. Appl. No. 09/452,516, mailed May 24, 2001, Office Action.
U.S. Appl. No. 09/452,516, mailed Oct. 19, 2001, Office Action.
U.S. Appl. No. 09/452,516, mailed May 20, 2002, Office Action.
U.S. Appl. No. 09/452,516, mailed Dec. 31, 2002, Office Action.
U.S. Appl. No. 09/452,516, mailed Apr. 11, 2003, Office Action.
U.S. Appl. No. 09/452,516, mailed Jul. 3, 2003, Office Action.
U.S. Appl. No. 09/452,516, mailed Jan. 13, 2004, Office Action.
U.S. Appl. No. 09/452,516, mailed Feb. 27, 2004, Office Action.
U.S. Appl. No. 09/452,516, mailed Apr. 22, 2004, Office Action.
U.S. Appl. No. 09/452,516, mailed Jul. 22, 2004, Office Action.
U.S. Appl. No. 09/452,516, mailed Jan. 18, 2005, Office Action.
U.S. Appl. No. 09/452,516, mailed Oct. 6, 2005, Office Action.
U.S. Appl. No. 09/452,516, mailed Mar. 13, 2006, Office Action.
U.S. Appl. No. 09/452,516, mailed May 30, 2006, Office Action.
U.S. Appl. No. 09/452,516, mailed Aug. 9, 2006, Office Action.
U.S. Appl. No. 09/452,516, mailed Oct. 23, 2006, Office Action.
U.S. Appl. No. 09/452,516, mailed Oct. 31, 2007, Office Action.
U.S. Appl. No. 09/452,516, mailed Mar 25, 2008, Office Action.
U.S. Appl. No. 09/452,516, mailed Sep. 30, 2008, Office Action.
U.S. Appl. No. 09/452,516, mailed Dec. 11, 2008, Office Action.
U.S. Appl. No. 09/452,516, mailed Jan. 12. 2009, Office Action.
U.S. Appl. No. 09/459,814, mailed Oct. 24, 2000, Office Action.
U.S. Appl. No. 09/459,814, mailed Apr. 25, 2001, Office Action.
U.S. Appl. No. 09/459,814, mailed Jul. 30, 2001, Notice of Allowance.
U.S. Appl. No. 09/498,695, mailed Jul. 19, 2000, Office Action.
U.S. Appl. No. 09/498,695, mailed Dec. 21, 2000, Office Action.
U.S. Appl. No. 09/498,695, mailed Mar. 16, 2001, Notice of Allowance.
U.S. Appl. No. 09/561,747, mailed Apr. 3, 2002, Office Action.
U.S. Appl. No. 09/561,747, mailed Sep. 26, 2002, Office Action.
U.S. Appl. No. 09/561,747, mailed Jan. 14, 2003, Office Action.
U.S. Appl. No. 09/561,747, mailed Jun. 4, 2003, Office Action.
U.S. Appl. No. 09/561,747, mailed Sep. 30, 2003, Office Action.
U.S. Appl. No. 09/561,747, mailed Nov. 3, 2003, Notice of Allowance.
U.S. Appl. No. 09/589,592, mailed Apr. 26, 2001, Office Action.
U.S. Appl. No. 09/589,592, mailed Nov. 9, 2001, Office Action.
U.S. Appl. No. 09/589,592, mailed Jan. 23, 2002, Notice of Allowance.
U.S. Appl. No. 09/589,592, mailed May 8, 2002, Notice of Allowance.
U.S. Appl. No. 09/589,592, mailed Aug. 7, 2002, Office Action.
U.S. Appl. No. 09/589,592, mailed Jan. 27, 2003, Office Action.
U.S. Appl. No. 09/589,592, mailed Jun. 4, 2003, Notice of Allowance.
U.S. Appl. No. 09/589,646, mailed Apr. 20, 2001, Office Action.
U.S. Appl. No. 09/589,646, mailed Feb. 13, 2002, Office Action.
U.S. Appl. No. 09/589,646, mailed May 14, 2002, Notice of Allowance.
U.S. Appl. No. 09/589,646, mailed Jul. 23, 2002, Notice of Allowance.
U.S. Appl. No. 09/752,212, mailed Apr. 24, 2002, Office Action.
U.S. Appl. No. 09/752,212, mailed Oct. 25, 2002, Office Action.
U.S. Appl. No. 09/752,212, mailed Feb. 28, 2003, Office Action.
U.S. Appl. No. 09/752,212, mailed Aug. 13, 2003, Office Action.
U.S. Appl. No. 09/752,212, mailed Oct. 29, 2003, Office Action.
U.S. Appl. No. 09/752,212, mailed Jan. 13, 2004, Office Action.
U.S. Appl. No. 09/752,212, mailed Feb. 24, 2004, Office Action.
U.S. Appl. No. 09/752,212, mailed Jun. 18, 2004, Notice of Allowance.
U.S. Appl. No. 09/882,930, mailed Oct. 7, 2002, Office Action.
U.S. Appl. No. 09/882,930, mailed Dec. 2, 2002, Notice of Allowance.
U.S. Appl. No. 09/884,432, mailed Sep. 16, 2002, Office Action.
U.S. Appl. No. 09/884,432, mailed Dec. 4, 2002, Office Action.
U.S. Appl. No. 09/884,432, mailed Mar. 25, 2003, Notice of Allowance.
U.S. Appl. No. 09/992,308, mailed Sep. 26, 2003, Office Action.
U.S. Appl. No. 09/992,308, mailed Dec. 31, 2003, Office Action.
U.S. Appl. No. 09/992,308, mailed Jun. 4, 2004, Office Action.
U.S. Appl. No. 09/992,308, mailed Sep. 27, 2004, Office Action.
U.S. Appl. No. 09/992,308, mailed Nov. 17, 2004, Office Action.
U.S. Appl. No. 10/021,528, mailed Dec. 10, 2002, Office Action.
U.S. Appl. No. 10/021,528, mailed Apr. 14, 2003, Notice of Allowance.
U.S. Appl. No. 10/155,910, mailed Oct. 6, 2003, Office Action.
U.S. Appl. No. 10/155,910, mailed May 5, 2004, Office Action.
U.S. Appl. No. 10/155,910, mailed Aug. 23, 2004, Notice of Allowance.
U.S. Appl. No. 10/264,619, mailed Jun. 14, 2005, Office Action.
U.S. Appl. No. 10/264,832, mailed Jan. 10, 2005, Office Action.
U.S. Appl. No. 10/264,832, mailed Oct. 20, 2005, Office Action.
U.S. Appl. No. 10/264,832, mailed Jan. 13, 2006, Office Action.
U.S. Appl. No. 10/264,832, mailed Apr. 7, 2006, Office Action.
U.S. Appl. No. 10/264,832, mailed Sep. 19, 2006, Office Action.
U.S. Appl. No. 10/291,930, mailed Mar. 3, 2004, Office Action.
U.S. Appl. No. 10/291,930, mailed Jun. 24, 2004, Notice of Allowance.
U.S. Appl. No. 10/291,930, mailed Oct. 4, 2005, Office Action.
U.S. Appl. No. 10/291,930, mailed Mar. 27, 2006, Office Action.
U.S. Appl. No. 10/291,930, mailed Sep. 22, 2006, Office Action.
U.S. Appl. No. 10/291,930, mailed Jan. 23, 2007, Office Action.
U.S. Appl. No. 10/299,524, mailed Mar. 3, 2004, Office Action.
U.S. Appl. No. 10/299,524, mailed Jun. 4, 2004, Offfice Action.
U.S. Appl. No. 10/327,371, mailed Apr. 15, 2010, Office Action.
U.S. Appl. No. 10/365,302, mailed Mar. 17, 2005, Office Action.
U.S. Appl. No. 10/365,302, mailed Oct. 4, 2005, Notice of Allowance.
U.S. Appl. No. 10/365,302, mailed Aug. 24, 2006, Office Action.
U.S. Appl. No. 10/365,302, mailed Mar. 29, 2007, Office Action.
U.S. Appl. No. 10/365,302, mailed Jun. 15, 2007, Office Action.
U.S. Appl. No. 10/365,302, mailed Dec. 12, 2007, Office Action.
U.S. Appl. No. 10/365,302, mailed Jul. 22, 2008, Office Action.
U.S. Appl. No. 10/365,302, mailed Dec. 9, 2008, Office Action.
U.S. Appl. No. 10/365,302, mailed Jun. 30, 2009, Office Action.
U.S. Appl. No. 10/365,302, mailed Jan. 15, 2010, Office Action.
U.S. Appl. No. 10/427,576, mailed Dec. 28, 2004, Office Action.
U.S. Appl. No. 10/427,576, mailed Sep. 14, 2005, Office Action.
U.S. Appl. No. 10/427,576, mailed Dec. 7, 2005, Office Action.
U.S. Appl. No. 10/427,576, mailed Apr. 26, 2006, Office Action.
U.S. Appl. No. 10/427,576, mailed Sep. 13, 2006, Office Action.
U.S. Appl. No. 10/427,576, mailed Mar. 7, 2007, Office Action.
U.S. Appl. No. 10/427,576, mailed May 31, 2007, Office Action.
U.S. Appl. No. 10/427,576, mailed Jul. 31, 2007, Office Action.
U.S. Appl. No. 10/427,576, mailed Dec. 10, 2007, Office Action.
U.S. Appl. No. 10/427,576, mailed Jul. 29, 2008, Office Action.
U.S. Appl. No. 10/427,576, mailed Apr. 3, 2009, Office Action.
U.S. Appl. No. 10/427,576, mailed Dec. 13, 2009, Office Action.

U.S. Appl. No. 10/668,401, mailed Sep. 1, 2005, Office Action.
U.S. Appl. No. 10/668,401, mailed Feb. 15, 2006, Office Action.
U.S. Appl. No. 10/668,401, mailed May 19, 2006, Office Action.
U.S. Appl. No. 10/668,401, mailed Aug. 23, 2006, Office Action.
U.S. Appl. No. 10/668,401, mailed Dec. 18, 2006, Office Action.
U.S. Appl. No. 10/668,401, mailed Apr. 30, 2007, Notice of Allowance.
U.S. Appl. No. 10/764,841, mailed Oct. 17, 2006, Office Action.
U.S. Appl. No. 10/764,841, mailed May 15, 2007, Office Action.
U.S. Appl. No. 10/764,841, mailed Oct. 31, 2007, Office Action.
U.S. Appl. No. 10/814,326, mailed Dec. 16, 2004, Office Action.
U.S. Appl. No. 10/814,326, mailed Sep. 6, 2005, Office Action.
U.S. Appl. No. 10/814,326, mailed Mar. 22, 2006, Office Action.
U.S. Appl. No. 10/900,632, mailed Feb. 21, 2007, Office Action.
U.S. Appl. No. 10/900,632, mailed May. 7, 2007, Office Action.
U.S. Appl. No. 10/900,632, mailed Jan. 3, 2008, Office Action.
U.S. Appl. No. 11/019,495, mailed May 7, 2008, Office Action.
U.S. Appl. No. 11/019,495, mailed Jan. 29, 2009, Office Action.
U.S. Appl. No. 11/019,495, mailed Sep. 15, 2009, Office Action.
U.S. Appl. No. 11/019,495, mailed Apr. 26, 2010, Office Action.
U.S. Appl. No. 11/437,710, mailed Sep. 10, 2008, Office Action.
U.S. Appl. No. 11/437,710, mailed Apr. 6, 2010, Office Action.
U.S. Appl. No. 11/723,339, mailed Mar. 28, 2008, Office Action.
U.S. Appl. No. 11/723,339, mailed Mar. 9, 2009, Office Action.
U.S. Appl. No. 11/723,339, mailed Jun. 23, 2009, Office Action.
U.S. Appl. No. 11/723,339, mailed Mar. 9, 2010, Office Action.
U.S. Appl. No. 11/783,565, mailed Mar. 31, 2009, Office Action.
U.S. Appl. No. 11/783,565, mailed Oct. 22, 2009, Office Action.
U.S. Appl. No. 11/870,262, mailed Apr. 24, 2009, Office Action.
U.S. Appl. No. 11/870,262, mailed Nov. 23, 2009, Notice of Allowance.
U.S. Appl. No. 11/870,262, mailed Mar. 23, 2010, Notice of Allowance.
U.S. Appl. No. 11/870,262, mailed Jul. 12, 2010, Notice of Allowance.
U.S. Appl. No. 12/369,360, mailed Mar. 26, 2010, Office Action.
U.S. Appl. No. 07/629,381, filed Dec. 18, 1990, Abrams.
U.S. Appl. No. 08/212,431, filed Mar. 11, 1994, Abrams.
U.S. Appl. No. 08/432,028, filed May 1, 1995, Abrams.
U.S. Appl. No. 08/527,650, filed Sep. 13, 1995, Abrams.
U.S. Appl. No. 09/452,516, filed Dec. 1, 1999, Boylan et al.
U.S. Appl. No. 09/572,352, filed May. 17, 2000, Pelton.
U.S. Appl. No. 09/992,308, filed Nov. 13, 2001, Anderson et al.
U.S. Appl. No. 10/264,619, filed Oct. 4, 2002, Boylan et al.
U.S. Appl. No. 10/264,832, filed Oct. 4, 2002, Boylan.
U.S. Appl. No. 11/129,319, filed May 16, 2005, Anderson et al.
ASTM Standard No. F2004-00 "Standard Test Method for Transformation Temperature of Nickel-Titanium Alloys by Thermal Analysis" (2000).
ASTM Standard No. F2082-01 "Standard Test Method for Determination of Transformation Temperature of Nickel-Titanium Shape Memory Alloys by Bend and Free Recovery" (2001).
Barrett, R., Titanium is Tops for Implants—but Too Dear for Some, Metal Bulletin Monthly, Oct. 1999, 346, pp. 48-53(abstract only).
Boylan, John F., "The Development of Radiopaque Nitinol," Guidant Corportion, Endovascular Solutions, Temecula, CA, pp. 1-6, proceedings from "The Shape Memory and Superelastic Technologies Conference" (SMST-2003), May 5-8, 2003, Asilomar Conference.
Buehler, W.J. And Cross W.B., "55-Nitinol Unique Wire Alloy with a Memory," Wire Journal, pp. 41- 49 (Jun. 1969).
Declaration by Sepehr Fariabi, dated Sep. 16, 1993.
Duerig, T.W. et al., Superelastic Nitinol for Medical Devices, Medical Plastics and Biomaterials Magazine, pp. 1-14, Mar. 1997.

Duerig, T.W. et al., Wide Hysteresis Shape Memory Alloys, Engineering Aspects of Shape Memory Alloys, pp. 130-136 (1990).
Enami et al., "Effect of W Addition on the Martensitic Transformation and Shape Memory Behavior of TiNi-Base Alloys," Journal De Physique IV, vol. 5-C8, pp. 629-633, (1995).
Funakubo, Hirayasu Shape memory alloys, edited by , 1984, pp. v-ix, 194, 195, 204-207, 256, 257, 266-269.
G.E. Dieter, Mechanical Metallurgy, 2nd edition, McGraw-Hill Book Co. pp. 204-208 (1976).
Hornbogen, E., Shape Memory: Three Usable Effects in One Material, DESIGN ENGINEERING, May 1990, pp. 67-73.
Jackson C.M H.J Wagner and R.J. Wasilewski, A Report 55-Nitinol-The Alloy with a Memory: Its Physical Metallurgy, Properties, and Applications:, prepared under contract for NASA by Battelle Memorial Institute, NASA-SP5110, Technology Utilization Office National Aeronautics and Space Administration, Washington, D.C., 1972, pp. 1-2 and 19-55.
Larousse Dictionary of Science and Technology, edited by Peter Walker, 1995, p. 1056.
Lin Z.C. et al., "The Study on Superlasticity of NiTiPt wire as a Function of Application Temperature," Technical Report, Guidant Corp., pp. 1-4 (Jun. 10, 2003).
Lindquist, "Structure and Transformation Behavior of Martensitic Ti-(Ni, pd) and Ti-(Ni,pt) Alloys," University of Illinois at Urbana—Champaign (1988).
Miyazaki, S. et al., Deformation and Transition Behavior Associated with the R-phase in NiTi alloys, Metallurgical Transactions A, vol. 17A, Jan. 1986, pp. 53-63.
Otsuka et al., "Shape Memory Effect," Shape Memory Materials, p. 41 (1998).
Poncin P., et al. "Stent Tubing: Understanding the Desired Attributes" Materials & Processes for Medical Devices Conference Sep. 8-10, 2003.
Proft et al., "The Mechanical Aspect of Constrained Recovery," Raychem Corp., pp. 115-129 (1985).
Quantities and Units of Measurement, A Dictionary and Handbook, J.V. Drazil, pp. 219, 236, and 246 (1983).
R.E. Reed-Hill, Physical Metallurgy Principals, D. Van Nostrand Co., Inc., Princeton New Jersey, pp. 231-234 (1964).
Russell, Scott M. et al., "Improved NiTi Alloys for Medical Applications," Proceedings of the Second International Conference on Shape Memory and Superelastic Technologies, pp. 429-436 (1997).
Stoeckel, D. et al., "Superelastic Ni-Ti Wire," Wire Journal International, pp. 45-50 (Mar. 1991).
U.S. Department of Commerce National Technical Information Service, Effects of Alloying Upon Certain Properties of 55.1 Nitinol, May 28, 1965.
Workshop on Fundamentals of Shape Memory and Workshop on Fundamentals of Shape Memory and Superelastic Alloys, (Ni-Ti Shape Memory Alloys Effects of Additions, chart only), International Organization on Shape memory and Superelastic Technologies, Asilomar, California (Mar. 6, 1994).
Yang, J.H. et al., "Stress-Induced Transformation and Superelasticity in Ni-Ti-Nb Alloys," Journal De Physique IV, pp. C8-771-C8-776 (Dec. 1995).
Zadno et al., Linear and non-linear superelasticity in Ni Ti, MRS (Materials Research Society) Int—l Meeting on Adv. Mats. vol. 9, pp. 200-206 (1989).
U.S. Appl. No. 10/427,576, mailed Aug. 30, 2010, Office Action.
U.S. Appl. No. 12/337,055, mailed Aug. 16, 2010, Office Action.
U.S. Appl. No. 09/705,422, mailed Oct. 25, 2010, Office Action.
U.S. Appl. No. 12/369,360, mailed Oct. 28, 2010, Office Action.
U.S. Appl. No. 11/870,262, mailed Nov. 15, 2010, Notice of Allowance.
U.S. Appl. No. 10/427,576, mailed Feb. 2, 2011, Notice of Allowance.

* cited by examiner

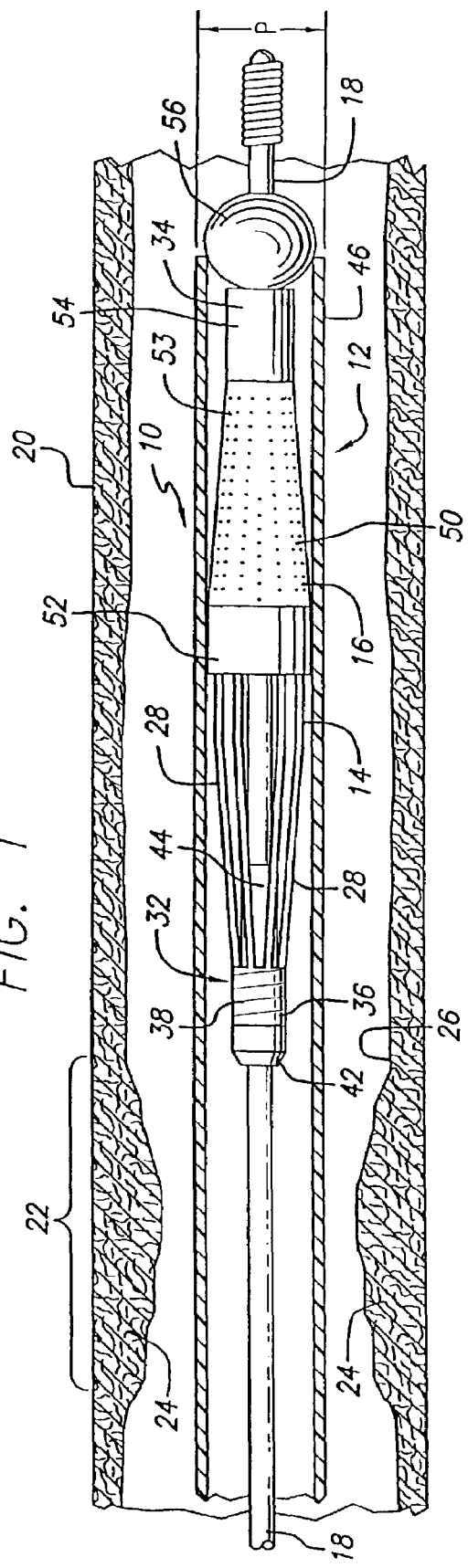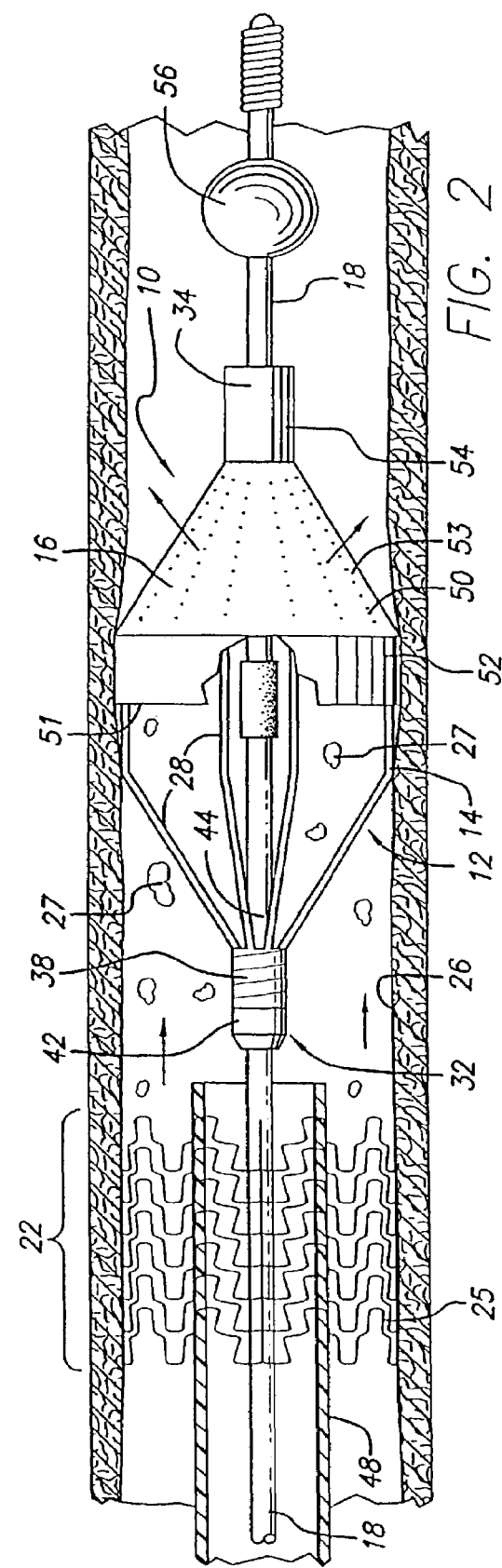

DEVICES CONFIGURED FROM HEAT SHAPED, STRAIN HARDENED NICKEL-TITANIUM

CROSS-REFERENCE TO RELATED APPLICATIONS

This is a continuation application of a application having U.S. Ser. No. 09/896,435, filed Jun. 29, 2001, now U.S. Pat. No. 6,602,272 which is a continuation-in-part of U.S. Ser. No. 09/705,422 filed Nov. 2, 2000, the contents of all of which are hereby incorporated by reference.

BACKGROUND OF THE INVENTION

The present invention relates generally to application of nickel-titanium alloys to medical devices. More precisely, the present invention is directed to cold worked nickel-titanium alloys that have pseudoelastic behavior without a phase transformation or onset of stress-induced martensite as applied to a medical device deployed from a sheath.

Near equi-atomic binary nickel-titanium alloys (nitinol) are known to exhibit "pseudoelastic" behavior when given certain cold working processes or cold working and heat treatment processes following hot working. Generally speaking, "pseudoelasticity" is the capacity of the nickel-titanium alloy to undergo large elastic strains on the order of 8 percent or more when stressed and to substantially fully recover all strain upon removal of the stress. Substantially full recovery is typically understood to be less than 0.5 percent unrecovered strain, also known as permanent set or amnesia.

Pseudoelasticity can be further divided into two subcategories: "linear" pseudoelasticity and "non-linear" pseudoelasticity. "Non-linear" pseudoelasticity is sometimes used by those in the industry synonymously with "superelasticity."

Linear pseudoelasticity results from cold working only. Non-linear pseudoelasticity results from cold working and subsequent heat treatment. Non-linear pseudoelasticity, in its idealized state, exhibits a relatively flat loading plateau in which a large amount of recoverable strain is possible with very little increase in stress. This flat plateau can be seen in the stress-strain hysteresis curve of the alloy. Linear pseudoelasticity exhibits no such flat plateau. Non-linear pseudoelasticity is known to occur due to a reversible phase transformation from austenite to martensite, the latter more precisely called "stress-induced martensite" (SIM). Linear pseudoelasticity has no such phase transformation associated with it. Further discussions of linear pseudoelasticity can be found in, for example, T. W. Duerig, et al., "Linear Superelasticity in Cold-Worked Ni—Ti," *Engineering Aspects of Shape Memory Alloys*, pp. 414-19 (1990).

Because of the useful nature of the nickel-titanium alloy, some have attempted to change its properties to solve different design needs. For example, U.S. Pat. No. 6,106,642 to DiCarlo et al. discloses annealing nitinol to achieve improved ductility and other mechanical properties. U.S. Pat. No. 5,876,434 to Flomenblit et al. teaches annealing and deforming nitinol alloy to obtain different stress-strain relationships.

Binary nickel-titanium alloys have been used in the medical field. Many medical device related applications exploit the non-linear pseudoelastic capabilities of nitinol. Examples include: U.S. Pat. Nos. 4,665,906; 5,067,957; 5,190,546; and 5,597,378 to Jervis; and U.S. Pat. Nos. 5,509,923; 5,486,183; 5,632,746; 5,720,754; and 6,004,629 to Middleman, et al.

Yet another application of nickel-titanium alloys is in an embolic protection or filtering device. Such embolic filtering devices and systems are particularly useful when performing balloon angioplasty, stenting procedures, laser angioplasty, or atherectomy in critical vessels, particularly in vessels such as the carotid arteries, where the release of embolic debris into the bloodstream can occlude the flow of oxygenated blood to the brain or other vital organs. Such an occlusion can cause devastating consequences to the patient. While the embolic protection devices and systems are particularly useful in carotid procedures, they are equally usefull in conjunction with any vascular interventional procedure in which there is an embolic risk. An embolic protection device that uses superelastic nitinol recently released to the market by the Cordis Corporation is known as the ANGIOGUARD.

What has been needed and heretofore unavailable in the prior art is a medical device that exploits the benefits of linear pseudoelastic nitinol. With the use of linear pseudoelastic nitinol, the mechanical strength of the device is substantially greater per unit strain than a comparable device made of superelastic nitinol. Furthermore, smaller component parts such as struts can be used because of the greater storage of energy available in a linear pseudoelastic nitinol device.

SUMMARY OF THE INVENTION

The present invention is generally directed to cold worked-nickel-titanium alloys that have linear pseudoelastic behavior without a phase transformation or onset of stress-induced martensite as applied to a medical device having a strut formed body deployed from a sheath.

In one preferred embodiment, the present invention is directed to a medical device for use in a body lumen comprising a body formed from struts, wherein the body includes a cold formed nickel-titanium alloy, and the nickel-titanium alloy is in a martensitic phase when the body is stressed into a first shape and also when the stress to the body is relieved to assume a second shape. Preferably, the transition temperature of the nickel-titanium alloy is set above 37 degrees C., body temperature.

The present invention further includes a sheath at least partially enveloping the body in its first shape. The sheath may be used to transport the device to a targeted location in the patient's anatomy, to deploy the device, and to retrieve the device at the end of the procedure.

The raw nitinol for use in the present invention has been cold formed and is further cold worked to set the desired expanded shape. Furthermore, the cold forming and cold working occur below the recrystallization temperature of the nitinol alloy.

During its operation, the linear pseudoelastic nitinol device can be stressed without developing stress-induced martensite in the alloy. Consistent with this behavior, an idealized stress-strain curve of the linear pseudoelastic nitinol does not contain any flat stress plateaus. Furthermore, despite application of stress, the nitinol alloy does not undergo a phase transformation from austenite to martensite or vice versa.

The resulting preferred embodiment device has greater mechanical strength at any given strain as compared to a device made of a standard superelastic nitinol. The present invention linear pseudoelastic nitinol device possesses more energy storage capacity as indicated by the stress-strain curve. As a result, for a given desired performance requirement, the present invention linear pseudoelastic nitinol device allows for smaller struts and consequently a lower profile useful in crossing narrow lesions.

Another advantage is that because the present invention uses linear pseudoelastic nitinol, the underlying alloy can be selected from a broader range of available materials yet still maintain consistent, mechanical properties. In other words, there is less sensitivity to material variations and processing vagaries as compared to superelastic nitinol. In addition, since the linear pseudoelastic nitinol has no transformation from martensite to austenite or vice versa, there is less of an influence by temperature-related effects.

There are many specific applications for the present invention including vena cava filters, septal plugs, just to name a few. One specific application for the present invention is in a filtering device and system for capturing embolic debris in a blood vessel created during the performance of a therapeutic interventional procedure, such as a balloon angioplasty or stenting procedure, in order to prevent the embolic debris from blocking blood vessels downstream from the interventional site. The devices and systems of the present invention are particularly useful while performing an interventional procedure in critical arteries, such as the carotid arteries, in which vital downstream blood vessels can easily become blocked with embolic debris, including the main blood vessels leading to the brain. When used in carotid procedures, the present invention minimizes the potential for a stroke occurring during the procedure. As a result, the present invention provides the physician with a higher degree of confidence that embolic debris is being properly collected and removed from the patient's vasculature during the interventional procedure.

An embolic protection device and system made in accordance with the present invention preferably includes an expandable filter assembly which is affixed to the distal end of a cylindrical shaft, such as a guide wire. The filter assembly includes an expandable strut assembly preferably made from a linear pseudoelastic nitinol, and includes a number of outwardly biased and extending struts that are capable of self-expansion from a contracted or collapsed position to an expanded or deployed position within a patient's vasculature. A filter element made from an embolic capturing media is attached to the expandable strut assembly. The filter element opens from a collapsed configuration to an expanded configuration via the movement of the expandable struts similar to that of an umbrella.

Other features and advantages of the present invention will become more apparent from the following detailed description of the invention when taken in conjunction with the accompanying exemplary drawings.

BRIEF DESCRIPTION OF THE DRAWINGS

FIG. 1 is a side elevational view, partially in cross-section, of an embolic protection device embodying features of the present invention showing the expandable filter assembly in its collapsed position within a restraining sheath and disposed within a vessel.

FIG. 2 is a side elevational view, partially in cross-section, similar to that shown in FIG. 1, wherein the expandable filter assembly is in its expanded position within the vessel.

DETAILED DESCRIPTION OF THE PREFERRED EMBODIMENTS

Figure 3:
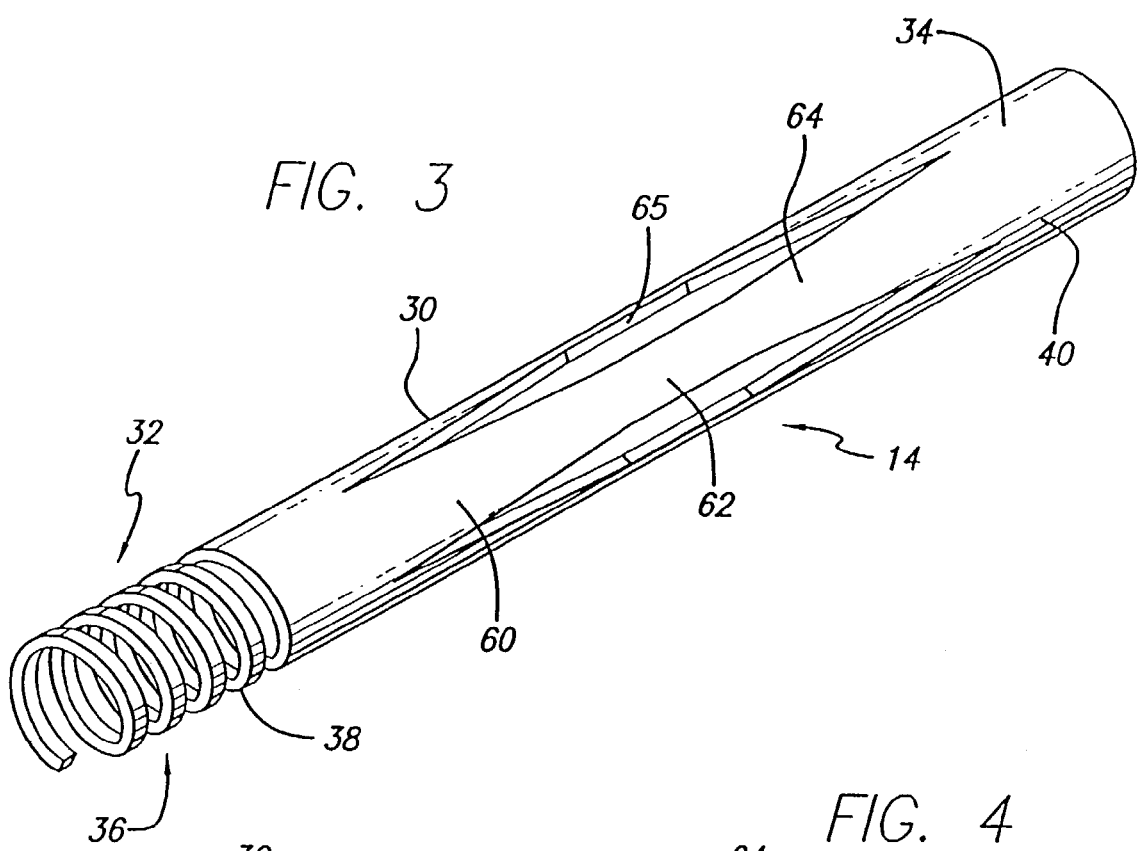
FIG. 3 is a perspective view of an expandable strut assembly which forms part of the filter assembly of the present invention as shown in its collapsed position.

The present invention is generally directed to cold worked nickel-titanium alloys that have linear pseudoelastic behavior without a phase transformation or onset of stress-induced martensite as applied to a medical device having a strut-formed body deployed from a sheath. Although the present invention is applicable to and contemplates numerous medical devices, for the sake of illustration, the following detail description focuses on an exemplary embodiment involving a filtering device and system for capturing embolic debris in a blood vessel created during the performance of a therapeutic interventional procedure.

In a preferred embodiment, the present invention medical device has a body formed from struts, wherein the body includes a cold formed nickel-titanium alloy, and the nickel-titanium alloy is in a martensitic phase when the body is stressed into a first shape and also when the stress on the body is relieved to assume a second shape. The preferred embodiment further includes a sheath at least partially enveloping the body in its first shape. The sheath may be used to transport the device to a targeted location in the patient's anatomy, to deploy the device, and to retrieve the device at the end of the procedure.

Turning now to the drawings, in which like reference numerals represent like or corresponding elements, FIGS. 1 and 2 illustrate a preferred embodiment embolic protection device 10 incorporating features of the present invention. In the particular exemplary embodiment shown in FIGS. 1 and 2, the embolic protection device 10 has a body identified as a filter assembly 12, which assembly includes an expandable strut assembly 14 and a filter element 16. The filter assembly 12 is rotatably mounted on the distal end of an elongated tubular shaft. The shaft as shown in FIGS. 1 and 2 is a guide wire 18, for example.

FIG. 1 also depicts a delivery system having a small delivery profile P. This reduced profile P is an advantage of the present invention filter assembly 14 and delivery system (restraining sheath 46 and recovery sheath 48), and is a result of the stress-strain hysteresis curve for linear pseudoelastic nitinol. This novel approach is described more fully below.

In the side elevational and cross-sectional views of FIGS. 1 and 2, the embolic protection device 10 is positioned within an artery 20 or other lumen of a patient. This portion of the artery 20 has an area of treatment 22 in which atherosclerotic plaque 24 has built up against the inside wall 26 of the artery 20. The filter assembly 12 is placed distal to, and downstream from, the area of treatment 22.

A balloon angioplasty catheter (not shown) can optionally be introduced within the patient's vasculature in a conventional Seldinger technique through a guiding catheter (not shown). The guide wire 18 is passed through the area of treatment 22 and the dilatation catheter can be advanced over the guide wire 18 within the artery 20 until the balloon portion is appositioned directly in the area of treatment 22. The balloon of the dilatation catheter is inflated, thereby expanding the plaque 24 against the inside wall 26 of the artery 20. This opens the occlusion, expands the artery 20, and reduces the blockage in the vessel caused by the plaque 24.

After the dilatation catheter is removed from the patient's vasculature, a stent 25 (shown in FIG. 2) may be delivered to the area of treatment 22 using over-the-wire techniques. The stent 25 helps to scaffold and maintain the area of treatment 22, which in turn help to prevent restenosis from occurring in the area of treatment 22.

Any embolic debris 27 that breaks off from the plaque 24 during the interventional procedure is released into the bloodstream. The embolic debris 27 is carried by blood flow (indicated by arrows) and is captured by the deployed, i.e., unfurled, filter element 16 of the filter assembly 12 located downstream from the area of treatment 22. Once the interventional procedure is completed, the filter assembly 12 is collapsed and removed from the patient's vasculature, taking with it all embolic debris 27 trapped within the filter element 16.

One exemplary embodiment of the expandable strut assembly 14 is shown in FIGS. 1-2. As can be seen in these figures, the expandable strut assembly 14 includes a plurality of radially expandable struts 28 that can move from a compressed or collapsed position as shown in FIG. 1 to an expanded or deployed position shown in FIG. 2. The expandable strut assembly 14 is preferably made from a linear pseudoelastic nitinol alloy so that the struts 28 have a radially outward bias toward the expanded position.

The expandable strut assembly 14 includes a proximal end 32 which is optionally rotatably attached to the guide wire 18. A distal end 34 is free to slide longitudinally along the guide wire 18 and can rotate thereabout. The distal end 34 translates along the guide wire 18 whenever the struts 28 move between the expanded and contracted positions. A proximal end 32 includes a short tubular segment or sleeve 36 which has a coil spring formed therein and which acts as a dampening member or element 38. The function of the dampening element 38 is explained below. The distal end 34 of the tubing 30 preferably includes a short segment or sleeve 40 which is slidably and rotatably disposed on the guide wire 18.

The filter element 16 in one preferred embodiment of the invention includes a tapered or cone shaped section 50, as seen in FIGS. 1 and 2. The filter element 16 optionally has a plurality of openings 53 that allow the blood to perfuse through (indicated by arrows), yet the openings 53 are small enough that the embolic debris 27 is captured inside the cone shaped section 50. The filter element 16 includes a short proximal section 52 which is integral with the cone shaped section 50 and expands to a substantially cylindrical shape when the struts 28 of strut assembly 14 are deployed. An inlet opening 51 located at the short proximal section 52 of cone shaped section 50 collects embolic debris 27, directing the debris 27 into the filter element 16.

The short proximal section 52 also functions as a superstructure to which the filter element 16 and the struts 28 of the strut assembly 14 can be adhesively or otherwise affixed. At the opposite end, the filter element 16 has a short distal cylindrical section 54 which is integral with the remaining sections of the filter element and is attached to the distal end 34 of the expandable strut assembly 14.

As best seen in FIG. 1, the filter assembly 12 is maintained in its collapsed or compressed position through the use of a restraining sheath 46. The restraining sheath 46 should have sufficient elasticity to resist the outward bias of the struts 28. One manner of achieving the required elasticity is through selection of the proper size and wall thickness for the sheath 46. Another is through use of the proper elastic material that has sufficient resilience to resist the expansive forces of the struts 28 held therein. Such sheath materials and designs are known in the art.

The guide wire 18 and the restraining sheath 46 have proximal ends (not shown) that extend outside of the patient. From outside the patient, it is possible to manipulate the struts 28 into the expanded position by retracting the restraining sheath 46 via its proximal end to expose the struts 28. Since the struts 28 are self-expanding by nature, the withdrawal of the restraining sheath 46 allows the struts 28 to spring open and the filter element 16 to unfurl into their expanded positions within the artery 20. This is depicted in FIG. 2.

The guide wire 18 optionally includes a small sphere 56 affixed thereto. The small sphere 56 is useful during the delivery of the embolic protection device 10 into the patient's vasculature. Specifically, the sphere 56 is approximately as large as the inner diameter of the restraining sheath 46 and is effectively used as a nose cone. The nose cone prevents possible "snowplowing" of the embolic protection device 10 as it is delivered through the patient's arteries.

When the embolic protection device 10 is to be removed from the patient's vasculature, an optional recovery sheath 48 is used to collapse and recover the filter assembly 12, as shown in FIG. 2. Generally, this recovery sheath 48 has a slightly larger inner diameter than the restraining sheath 46 since the struts 28 are now deployed. Furthermore, the recovery sheath 48 must have sufficient tensile strength and elasticity at the distal end 47 to be capable of collapsing the expanded strut assembly 14.

The collapse of the expandable strut assembly 14 can be accomplished by holding the guide wire 18 and moving the proximal end (not shown) of the recovery sheath 48 forward, which moves the distal end 47 of the sheath 48 over the struts 28. Alternatively, the recovery sheath 48 can be held stationary while the proximal end of the guide wire 18 is retracted back to pull the entire filter assembly 12 into the sheath 48. Upon collapse of the filter assembly 12, any embolic debris 27 generated and entering the bloodstream during the interventional procedure remains trapped inside the filter element 16 and is withdrawn from the bloodstream when the embolic protection device 10 is removed from the patient's vasculature.

The number of struts 28 formed on the expandable strut assembly 14 can be any number which provides sufficient expandability within the artery to properly deploy and maintain the filter element 16 in place. In the embodiment shown in FIGS. 1 and 2, the expandable strut assembly has four self-expanding struts 28. Likewise, the particular size and shape of each strut 28 can be varied.

Figure 4:
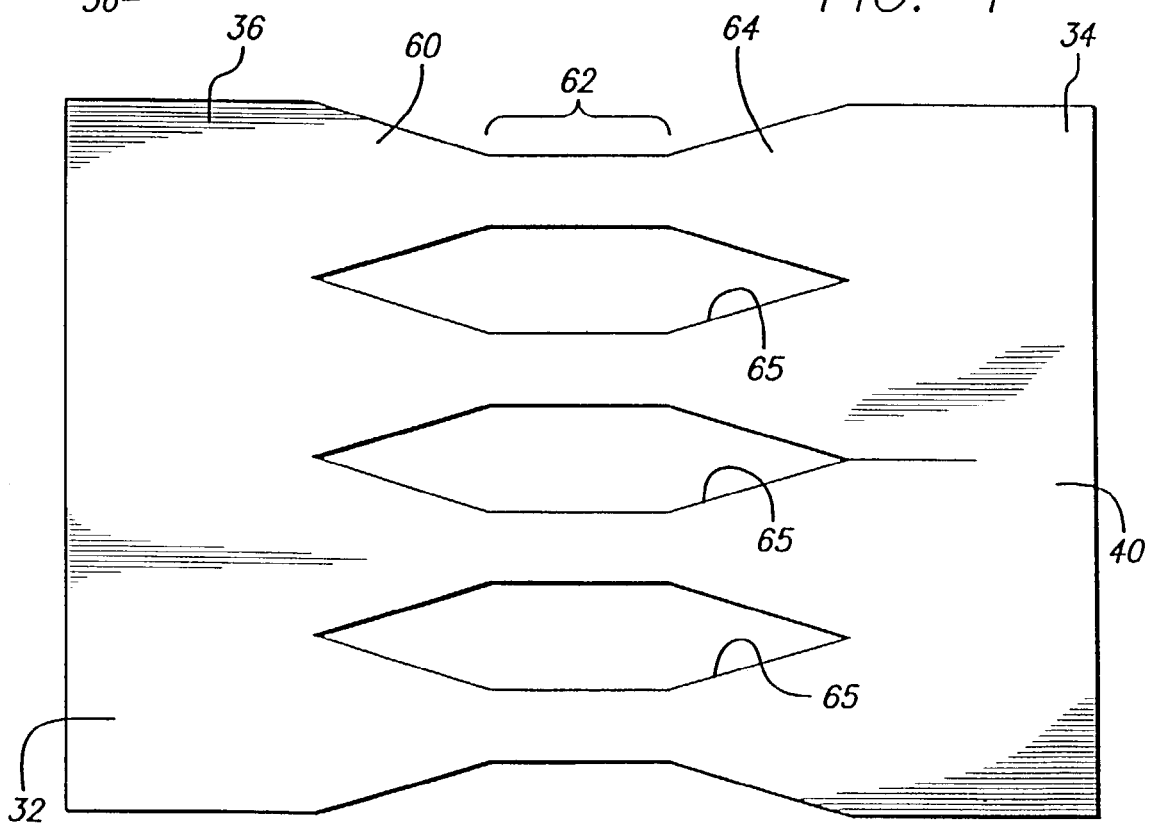
FIG. 4 is a plan view of a flattened section of the expandable strut assembly shown in FIG. 3 which illustrates one particular strut pattern.

FIGS. 3-4 show an expandable strut assembly 14 having a strut pattern formed from an inverted, triangular shape first portion 60, a substantially straight center section 62, and a second inverted triangular shaped section 64, which completes the strut. This particular strut pattern is one preferred design that provides greater strength in regions of the strut where there would be a tendency for the strut to break or become weakened. These regions include the very proximal and distal ends of each strut which are designed with a wider base. This particular design also allows the expandable strut assembly 14 to open and close more uniformly. This is advantageous especially when collapsing the struts for removal from the patient. Additionally, the center section 62 allows the struts 28 to expand to a greater volume, which allows a larger filter element to be placed on the strut assembly 14, if needed.

When the precise pattern is cut into the tubing 30, a sleeve 36 which forms the proximal end 32 may optionally be formed into a helical coil as shown in FIG. 3. The helical coil then functions as a damping element 38 for the expandable strut assembly 14. As seen in FIGS. 1 and 2, the sleeve 36 slides over the guide wire 18. The proximal end 32 of the expandable strut assembly 14 is mounted between a tapered fitting 42 and an optional radiopaque marker band 44. The tapered end fitting 42 and the marker band 44 affix the proximal end 32 on to the guide wire 18 to prevent any longitudinal motion, yet allow for rotation of the filter assembly 12.

FIG. 4 is a plan view of a rolled out flat sheet of the tubing 30 used to form the struts 28. Preferably, however, the tubing 30 is made from nitinol and the initial state of the tubing is fully martensitic in the as-received condition. A particular design pattern is cut into the thin wall of the tubing 30 in order to form each strut. In the case of the exemplary embodiment shown in FIG. 3, that pattern consists of truncated diamond shape apertures 65 which help form the first section 60, the center section 62 and the triangular shaped section 64. To create the apertures 65, portions of the tubing 30 are selectively removed through laser cutting preferably, but etching, stamping, or other processes are suitable insofar as each particular strut can be fashioned into a precise shape, width, and length. This truncated diamond aperture pattern 68 repeats, as seen in FIG. 4, to provide uniform size to each of the struts 28 formed therein. Narrow struts such as that shown in FIGS. 1 and 2 can, of course, be formed as described above.

Subsequently, the laser cut nitinol tubing 30 is preferably cold formed and specifically cold worked with no heat treatment such that it remains in the fully martensitic state. The cold working proceeds only at temperatures below the recrystallization temperature of the nitinol alloy. Next, the laser-cut nitinol tubing 30 is cold worked to its desired expanded size. The desired expanded size is thus imparted or set into the laser cut tube.

Importantly, the laser-cut nitinol tubing 30 is not heat treated to prevent generation of any loading or unloading plateaus in the stress-strain curve. In an alternative embodiment, the nitinol tubing may undergo heat treating for only very limited durations at low temperatures. The present invention recognizes that a significant difference between linear pseudoelasticity and non-linear pseudoelasticity is the absence or presence, respectively, of stress-induced martensite. It also recognizes that in order to set a particular shape in nitinol, the nitinol must be heat treated at a relatively high temperature for a short period of time. Under normal circumstances, this material would then exhibit non-linear pseudoelasticity and therefore would undergo a reversible phase transformation from austenite to martensite. When setting a shape under standard conditions, for example, 550 degrees C. for 5 minutes, the nitinol exhibits essentially no springback; that is, its unconstrained shape after heat treatment is nearly identical to its constrained shape during heat treatment. The nitinol does not spring back to its original shape prior to heat treatment. At the other extreme, linear pseudoelastic nitinol with no heat treatment has 100 percent springback and always returns to its original, cold worked shape.

Springback is a continuous function between no heat treatment (100 percent springback) and ideal shape setting heat treatment (approximately zero percent springback). From an engineering perspective for design of nitinol based pseudoelastic devices, less springback is more favorable than more springback. However, in some circumstances, linear pseudoelasticity may be preferable to non-linear pseudoelasticity. Therefore, the present invention, in addition to contemplating cold-worked only nitinol, addresses that regime of heat treatment temperatures and times within which springback is adequately minimized to successfully impart a desired shape to the nitinol structure and within which the nitinol does not develop a stable and reversible martensitic phase.

In the preferred embodiment of the present invention, to achieve the linear pseudoelastic behavior, the binary nickel-titanium tubing has approximately 55.8 weight percent nickel. The tubing must contain a minimum of approximately 38 percent cold working when measured by the reduction in cross-sectional area, and there is not to be any heat treatment following final cold reduction. As to the alternative embodiment, the present invention contemplates accumulated heat treatment of the tubing of up to 350 degrees C. for up to 5 minutes. Under ideal conditions, these process parameters should adequately ensure that the nitinol remains martensitic without a phase change under stress.

In one preferred embodiment, a transformation temperature of the nitinol is set above a typical human body temperature of 37 degrees C. Preferably, the transformation temperature is measured by the austenite finish temperature ($A_f$); of course, other transformation temperatures such as the austenite start temperature ($A_s$), the martensite start temperature, ($M_s$), or the martensite finish temperature ($M_f$) can be used as the defining metric. It is understood that the austenite finish temperature ($A_f$) is defined to mean the temperature at which the material completely reverts to austenite. The $A_f$ is ideally determined by a Differential Scanning Calorimeter (DSC) test, known in the art. The DSC test method to determine transformation temperatures for a nitinol ingot is guided by ASTM standard no. F2004-00, entitled "Standard Test Method for Transformation Temperature of Nickel-Titanium Alloys by Thermal Analysis," or by an equivalent test method known in the art.

Alternatively, the "active $A_f$" for a tubing used to manufacture the embolic protection device or other medical device is determined by a bend and free recovery test, also known in the art. In such a test, the tubing is cooled to under the $M_f$ temperature, deformed, and warmed up. While monitoring the increasing temperature, the point of final recovery of the deformation in the tubing approximates the $A_f$ of the material. The active $A_f$ testing technique is guided by ASTM standard no. F2028-01, entitled "Standard Test Method for Determination of Transformation Temperature of Nickel-Titanium Shape Memory Alloys by Bend and Free Recovery," or by an equivalent test method known in the art.

The $A_s$ or $A_f$ of a nitinol material can be adjusted by various methods known in the art. For example, changing the composition of nickel to titanium, cold working the material, use of a ternary or a quaternary element, all affect the transformation temperature. Examples of ternary elements that may be alloyed with nickel-titanium include iridium, platinum, gold, rhenium, tungsten, palladium, rhodium, tantalum, silver, ruthenium, or hafnium. Accordingly, when the present invention medical device is used within a mammalian body which is approximately 37 degrees C., having the $A_s$ or $A_f$ set above that body temperature insures that the device remains in the martensitic phase throughout its use within the body. Insofar as the martensitic phase is maintained as described, the nickel-titanium alloy exhibits only linear pseudoelasticity when the medical device encounters operating stresses. Thus, by operating in this martensitic range, it is possible to exploit the beneficial properties of a linear pseudoelastic nickel-titanium alloy. These beneficial properties are described elsewhere, but include much greater reversible strain as compared to a stainless steel, and greater strength as compared to operating in a non-linear pseudoelastic range.

Figure 5:
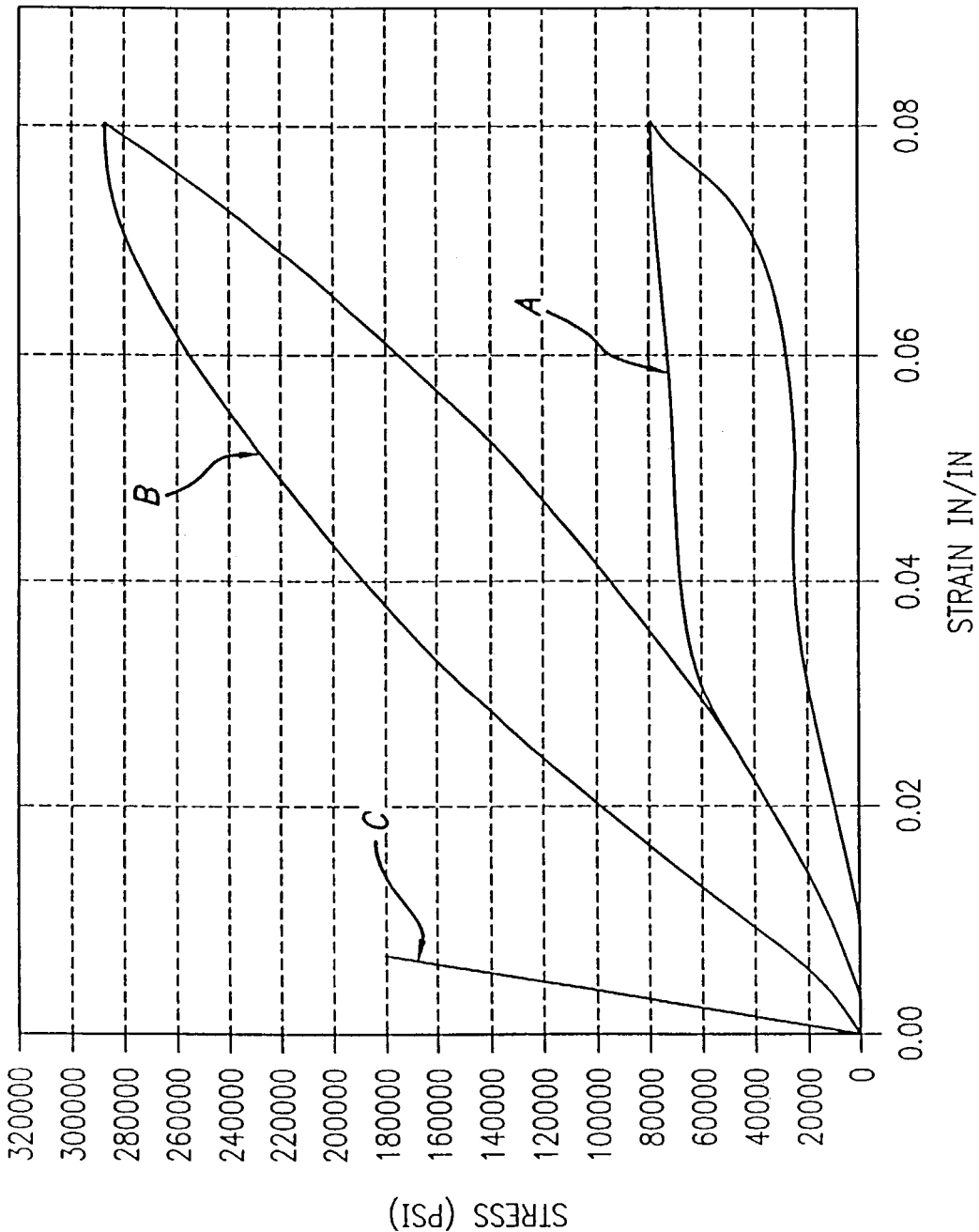
FIG. 5 is a set of stress-strain curves for conventional 316L stainless steel, linear pseudoelastic nitinol, and non-linear pseudoelastic nitinol.

To illustrate the foregoing points, FIG. 5 contains the elastic component of three idealized stress-strain curves for 316L stainless steel, linear pseudoelastic nitinol, and non-linear pseudoelastic nitinol. In a preferred embodiment, the expandable strut assembly 14 of the present invention is formed partially or completely of alloys such as the linear pseudoelastic nitinol shown in FIG. 5.

In FIG. 5, in an idealized curve A for a non-linear pseudoelastic nitinol, the relationship is plotted on x-y axes, with the x axis representing strain and the y axis representing stress. The x and y axes are labeled in units of stress from zero to 320 ksi and strain from 0 to 9 percent, respectively.

In curve A, when stress is applied to a specimen of a metal such as nitinol exhibiting non-linear pseudoelastic characteristics at a temperature at or above that which the transformation of the martensitic phase to the austenitic phase is complete, the specimen deforms elastically until it reaches a particular stress level where the alloy then undergoes a stress-induced phase transformation from the austenitic phase to the martensitic phase (i.e., the stress-induced martensite phase).

As the phase transformation progresses, the alloy undergoes significant increases in strain with little or no corresponding increases in stress. On curve A this is represented by upper, nearly flat stress plateau at approximately 70 to 80 ksi. The strain increases while the stress remains essentially constant until the transformation of the austenitic phase to the martensitic phase is complete. Thereafter, further increase in stress is necessary to cause further deformation. The martensitic metal first yields elastically upon the application of additional stress and then plastically with permanent residual deformation (not shown).

If the load on the specimen is removed before any permanent deformation has occurred, the martensite specimen elastically recovers and transforms back to the austenitic phase. The reduction in stress first causes a decrease in strain. As stress reduction reaches the level at which the martensitic phase transforms back into the austenitic phase, the stress level in the specimen remains essentially constant (but less than the constant stress level at which the austenitic crystalline structure transforms to the martensitic crystalline structure until the transformation back to the austenitic phase is complete); i.e., there is significant recovery in strain with only negligible corresponding stress reduction. This is represented in curve A by the lower stress plateau at about 20 ksi.

After the transformation back to austenite is complete, further stress reduction results in elastic strain reduction. This ability to incur significant strain at relatively constant stress upon the application of a load and to recover from the deformation upon the removal of the load is commonly referred to as non-linear pseudoelasticity (or superelasticity).

FIG. 5 also has a curve B representing the idealized behavior of linear pseudoelastic nitinol as utilized in the present invention. Curve B generally has a higher slope or Young's Modulus than curve A for the non-linear pseudoelastic nitinol. Also, curve B does not contain any flat plateau stresses found in curve A. This stands to reason since the nitinol of curve B remains in the martensitic phase throughout and does not undergo any phase change. The same tension and release of stress cycle to generate curve A is used to generate curve B. To that end, curve B shows that increasing stress begets a proportional increase in reversible strain, and a release of stress begets a proportional decrease in strain. The areas bounded by curves A and B represent the hysteresis in the nitinol.

As apparent from comparing curve B to curve A in FIG. 5, with the use of linear pseudoelastic nitinol, the mechanical strength of the present invention medical device is substantially greater per unit strain than a comparable device made of superelastic nitinol. Consequently, a major benefit is that smaller component parts such as struts can be used because of the greater storage of energy available in a linear pseudoelastic nitinol device. A small profile is one critical factor for crossing narrow lesions or for accessing remote and tortuous arteries.

FIG. 5 includes curve C which is the elastic behavior of a standard 316L stainless steel. Stress is incrementally applied to the steel and, just prior to the metal deforming plastically, decrementally released. It is provided here simply for comparison to curves A and B.

As mentioned above, the present invention medical device uses preferably a binary nickel-titanium alloy. In an alternative embodiment, however, the nickel-titanium may be alloyed with a ternary element such as palladium, platinum, chromium, iron, cobalt, vanadium, manganese, boron, copper, aluminum, tungsten, tantalum, or zirconium.

While the present invention has been illustrated and described herein in terms of linear pseudoelastic nitinol filter assembly of an embolic protection device and its delivery system, it is apparent to those skilled in the art that the present invention can be used in other instances. Other modifications and improvements may be made without departing from the scope of the present invention.

What is claimed is:

1. An embolic protection filter system for use in a body lumen, comprising:
    a tubular body with self-expanding struts having a compressed state and an expanded state;
    the tubular body including a nickel-titanium alloy, wherein said nickel-titanium alloy:
        further comprises platinum;
        has a transformation temperature greater than about 37 degrees C.; and
        is always in the martensitic phase and exhibits linear pseudoelasticity when deployed with the body lumen;
    a shaft extending distally from a distal end of the tubular body; and
    a filter element joined to the tubular body, the filter element extending proximally from a shaft distal end, the filter element configured to expand radially outwardly from the shaft and extend about a portion of the shaft when the self-expanding struts of the tubular body are in the expanded state.

2. The embolic filter system of claim 1, wherein the system includes a sheath at least partially overlying and holding the tubular body in a compressed state and maintaining the tubular body in the martensitic phase.

3. The embolic filter system of claim 1, wherein a Young's Modulus for the linear pseudoelastic nickel-titanium alloy is less than steel and greater than non-linear pseudoelastic nickel-titanium.

4. The embolic filter system of claim 1, wherein the shaft comprises a guidewire.

* * * * *